United States Patent
Kopylov et al.

(10) Patent No.: US 6,814,757 B2
(45) Date of Patent: Nov. 9, 2004

(54) JOINT SURFACE REPLACEMENT OF THE DISTAL RADIOULNAR JOINT

(75) Inventors: Philippe Kopylov, Lund (SE); Magnus Tagil, Lund (SE); William F. Ogilvie, Austin, TX (US)

(73) Assignee: Ascension Orthopedics, Inc., Austin, TX (US)

( * ) Notice: Subject to any disclaimer, the term of this patent is extended or adjusted under 35 U.S.C. 154(b) by 61 days.

(21) Appl. No.: 10/251,896

(22) Filed: Sep. 20, 2002

(65) Prior Publication Data

US 2003/0135280 A1 Jul. 17, 2003

Related U.S. Application Data

(63) Continuation-in-part of application No. PCT/SE01/00615, filed on Mar. 22, 2001.

(30) Foreign Application Priority Data

Mar. 23, 2000 (SE) .............................................. 0001024

(51) Int. Cl.[7] .................................................. A61F 2/42
(52) U.S. Cl. .................................................. 623/21.11
(58) Field of Search ............... 623/21.11, 21.12–21.17, 623/16.11, 17.19, 18.11, 21.18, 20.11, 20.12, 20.13, 21.19, 20.18

(56) References Cited

U.S. PATENT DOCUMENTS

| 4,224,695 | A | * | 9/1980 | Grundei et al. ........... 623/20.12 |
| 5,108,444 | A | * | 4/1992 | Branemark .............. 623/21.12 |
| 5,133,762 | A | * | 7/1992 | Branemark .............. 623/21.12 |
| 5,358,529 | A | | 10/1994 | Davidson ..................... 623/20 |
| 5,782,923 | A | * | 7/1998 | Engelbrecht et al. .... 623/20.13 |
| 5,879,386 | A | * | 3/1999 | Jore ......................... 623/16.11 |
| 5,879,395 | A | * | 3/1999 | Tornier et al. ........... 623/20.13 |
| 5,951,604 | A | | 9/1999 | Scheker ........................ 623/21 |
| 6,017,366 | A | * | 1/2000 | Berman .................... 623/21.11 |
| 6,051,751 | A | * | 4/2000 | Sioshansi et al. ........... 128/898 |
| 6,059,832 | A | * | 5/2000 | Menon .................... 623/21.15 |
| 6,302,915 | B1 | * | 10/2001 | Cooney et al. .......... 623/21.12 |
| 6,342,075 | B1 | * | 1/2002 | MacArthur .............. 623/20.14 |
| 6,379,387 | B1 | * | 4/2002 | Tornier .................... 623/20.12 |

FOREIGN PATENT DOCUMENTS

| EP | 0749735 A1 | * | 6/1995 | .............. 623/21.11 |
| FR | 2673100 A1 | * | 8/1992 | .............. 623/21.11 |
| GB | 2269752 A | * | 2/1994 | .............. 623/21.11 |

* cited by examiner

*Primary Examiner*—Alvin Stewart
(74) *Attorney, Agent, or Firm*—Fitch, Even, Tabin & Flannery

(57) ABSTRACT

A joint surface replacement or joint prosthesis for the distal radioulnar (DRU) joint. A complete surface replacement comprises two parts, a radial component (1) and an ulnar component (2), both of which are designed to be inserted radially relative the radius (6) and the ulna (7). The radial (1) and ulnar (2) components are constructed to assure that the concave surface of the radial component may be pivoted and translated around the convex surface of the ulnar component during rotational movement of the forearm. Either component may be singularly implanted when there is no deterioration of the mating component. By providing these components in a range of thicknesses and lengths, more effective stabilization of such joint is possible.

19 Claims, 9 Drawing Sheets

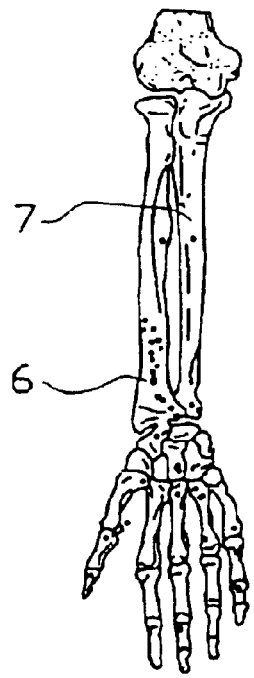
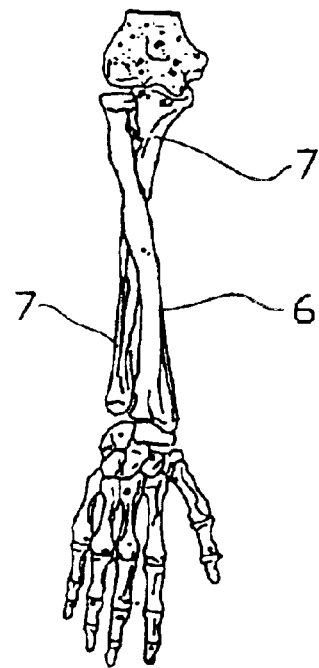
Fig.5a  Fig.5b
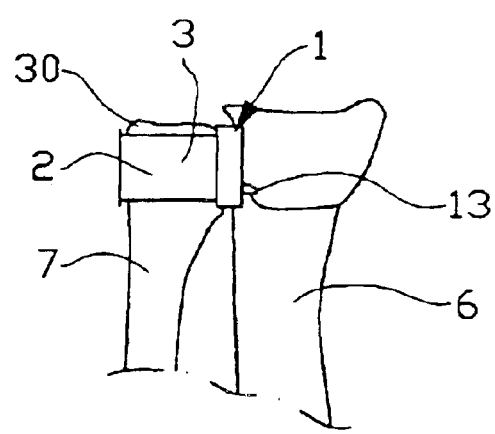
Fig.6a

JOINT SURFACE REPLACEMENT OF THE DISTAL RADIOULNAR JOINT

This application is a continuation-in-part of international application PCT/SE01/00615, filed Mar. 22, 2001, which designated the United States and was published in English as WO 01/70138, and which claimed priority from Swedish application Serial No. 0001024-9, filed Mar. 23, 2000.

BACKGROUND

The present invention relates to a joint prosthesis, sometimes termed a surface replacement, for the distal radioulnar (DRU) joint of the forearm.

Cartilage destruction of the distal radioulnar joint is often caused by disease, such as different types of inflammatory diseases, especially rheumatoid arthritis. Today these injuries are frequently operated rather late in the evolution of the disease when pain evolves or mobility starts to decrease. At this time, the joint is most often destroyed, with little remaining cartilage and with varying degrees of bone destruction. A operation commonly used is the Darrach procedure, which consists of a simple resection of the ulnar head (caput ulna). The cut ulnar bone-end is now mobile and "floats" and sometimes the wrist feels unstable and painful. There is a risk for the ulna and radius to stick to each other. Sometimes the patient feels a clicking sensation, sometimes painful, when turning the forearm. Another potential consequence of rheumatoid arthritis is destruction of the ligaments, joint capsule or other connective tissue stabilizers crossing the DRU joint. A tear or weakening of these structures, such as the distal radioulnar ligaments and the interosseus membrane, as a result of rheumatoid diseases can also compromise the stability of the DRU joint because of the loss of tension in the radioulnar ligaments. Such loss of ligament tension may allow the DRU joint to sublux or dislocate.

In non-rheumatoid patients, the DRU joint may often be injured as a consequence of a distal radial fracture and by a tear in the distal radioulnar ligaments or interosseus membrane, causing a secondary joint surface incongruity or instability of the distal radial ulnar joint. Such an incongruity may also occur as a consequence of an intraarticular radial fracture extending into the DRU joint; as a result, the joint surface may heal with a step-off causing an incongruity. Also a radial fracture, which does not extend into the DRU joint, might influence the congruity due to an angulation of the radial shaft and the radial joint surface of the DRU joint. A distal radioulnar ligament tear might also compromise the stability of the DRU joint as a consequence of loss of tension in the radioulnar ligaments or interosseus membrane, and such a loss of ligament tension may allow the DRU joint to sublux or dislocate.

The consequence of an incongruity may be an osteoarthritis, which may be symptomatic. Different treatment alternatives exist, none of them being particularly good. All are compromises, trading different wrist and hand functions to achieve pain relief. A common method is the Sauvee-Kapandjii procedure, where the ligaments from the ulnar tip to the radius and carpus are maintained, the ulna is resected proximally and screws are used to keep the ulnar head in contact with the radius. The radius together with the ulnar head then pivot, within the osteotomy defect. Other known methods include the Bowers hemiresection of the ulnar end with soft tissue interposition and the Watson distal ulnar resection. Another method resects the ulnar head and replaces it with a prosthesis.

An object of the present invention is to develop a device to make it possible to use a method of operation which would lead to better clinical results than the various methods in use today.

Another object of the invention is to make it possible to keep the DRU joint as intact as possible through a device, that allows resurfacing the articular surfaces of the distal portion(s) of radius and/or ulna bone(s) that form the DRU joint without disturbing the ligaments and their attachment sites that stabilize the DRU joint.

It is also an object of the invention to make it possible to stabilize an unstable DRU joint by providing a means to adjust the tension, generally to increase it, of the distal radioulnar ligaments and the interosseus membrane. A surgeon, after having prepared the implantation site, will be able to adjust the tension of the stabilizing structures, such as the distal radioulnar ligaments or interosseus membrane. This can be done by increasing or decreasing the distance between the radius and ulna by selecting component(s) of appropriate size and thickness.

It is a further object of the invention to make it possible to employ only the radial or ulnar component of the device (sometimes termed a hemi implantation), to resurface only the articular surface of the distal radius or the distal ulna respectively, if the clinical findings are such that the destruction of the articular surfaces of the DRU joint is confined exclusively to either the radius or the ulna. The device, i.e. the radial or ulnar component, when used as hemi implant, allows adjustment of the tension of the distal radioulnar ligament by selecting an appropriate size device.

Yet another object of the invention is to provide a means to resurface two distinct types of ulnar DRU joint cartilage damage. One embodiment of the ulnar component of the present invention provides a means to resurface only the distal lateral region of the ulna that is the site of articular cartilage in a physiologic DRU joint. This distal lateral region of the distal ulna articulates against the ulnar notch of the radius. A second embodiment of the ulnar component of the present invention provides a means to resurface both the distal lateral region of the ulna and the portion of the distal end of the ulna facing the TFCC and the lunate bone, which are sites where there is articular cartilage.

A device according to the invention can be used following a radial fracture, or the onset of rheumatoid arthritis or other rheumatoid disease involving the distal radioulnar joint. The prosthesis generally supports the turning (pronation/supination) motion of the forearm. The ulna is the non-moving and weight-bearing fundament of the distal radioulnar joint, while the radius is the mobile component, with mostly compressive forces influencing its positioning during its turning movement. The radius turns around the ulnar head. Besides the distal joint surfaces between the radius and ulna, a prerequisite for the turning movement is the existence of joint surfaces proximally in the elbow. The proximal radioulnar joint consists of the radial head and the ulna with a fossa radii and an annular ligament.

In the elbow, the ulna makes a flexion or extension motion, whereas the radius rotates around an axis which passes through the proximal head of the radius and the distal head of the ulna. Both the radius and the ulna have such a curvature that the middle points of the two bones are fairly far away from each other. Through this arrangement, the radius has enough space to be able to rotate around the ulna.

Stability depends both on the congruity of the two radioulnar joints as well as on the ligaments of the two joints keeping the radius and ulna together. Muscles forces push the two bones together, still allowing them to make both a rolling and a translatory motion relative each other. The forces in the distal radioulnar joint thus are mainly compressive. Different parts of the ulnar head will be in contact with the joint surface of the radius as the ulnar head successively translates and rotates along the joint surface. In the two extreme positions of pronation and supination, the joint surface of the radius is loaded in the volar part and the dorsal part respectively. The distal radioulnar joint ligaments stop the joint from luxation, and secondarily, the joint is stabilized by the interosseus membrane When problems arise in the distal radioulnar joint, it is common, as previously mentioned, to simply resect the ulnar head and attach it to the radius or to replace it with a prosthesis. The result of such treatment is often that the distal position of the radius becomes changed (because the radius is resting upon the ulna) and such a change of position may often makes the result of the operation less than satisfactory.

In contrast, through an implantation of a surface replacement according the present invention, the ulna is kept intact; thus it is able to support the radius without changing the position of the radius in an unfavourable way.

Generally surface replacements embodying various features of the invention make it possible to achieve the above-mentioned objects and demands. Moreover, the invention makes it possible to preserve the ligamentous apparatus when implanting a surface replacement. This means that the compressive forces within the distal radioulnar joint are maintained after the operation and contribute to the stabilization of the joint. By using appropriate of the different component sizes which are available, the invention further makes it possible, in cases where certain stabilizing ligaments are destroyed by disease or injury, to adjust the tension of the remaining stabilizing structures in order to get a stabile joint.

BRIEF DESCRIPTION OF THE DRAWINGS

The invention will be described in more detail by reference to the following drawings wherein:

FIG. 6a is a schematic figure showing the anchorage of a complete surface replacement using components of the invention;

FIG. 6b shows an example of a position of the radial and ulnar components relative each other after implantation in a distal radioulnar joint as shown in FIG. 6a;

FIG. 7b is a side view taken through along section line VII—VII of FIG. 7a;

FIG. 8b shows the ulnar component, according to FIG. 8, as seen in the direction of the arrow B in FIG. 8a;

Figure 1:
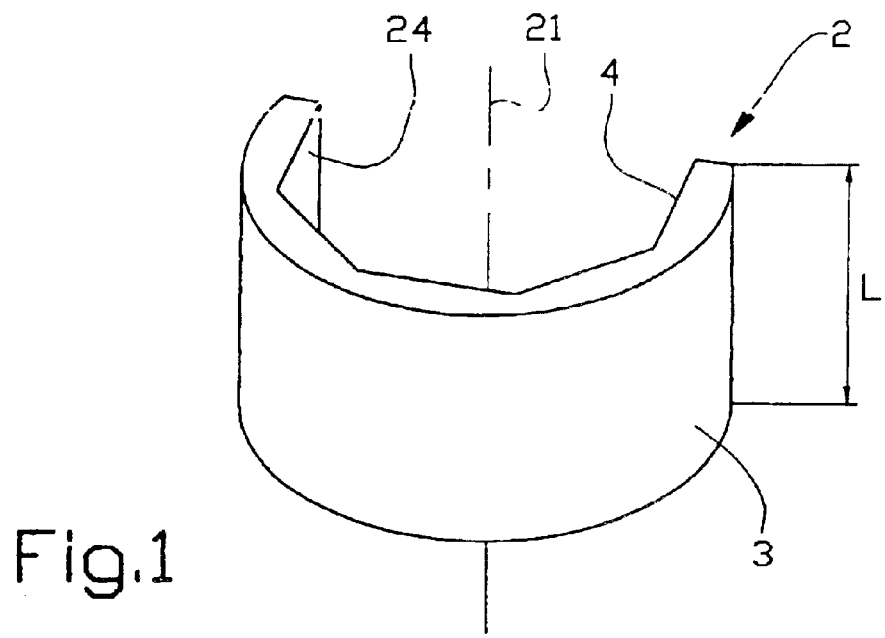
FIGS. 1 and 2 show an ulnar component embodying various features of the invention in two different perspectives.

A complete surface replacement according to the invention comprises two parts, a radial component (1,1a) and an ulnar component (2,2a). When implanted, the two components 1 and 2 are mounted on radial surfaces on the radius (6) and the ulna (7), respectively. The expression "radial mounting" in this description means that, during the operation, the two artificial components are placed at facing side surfaces of the natural joint components and form a new articulating surface.

Figure 8:
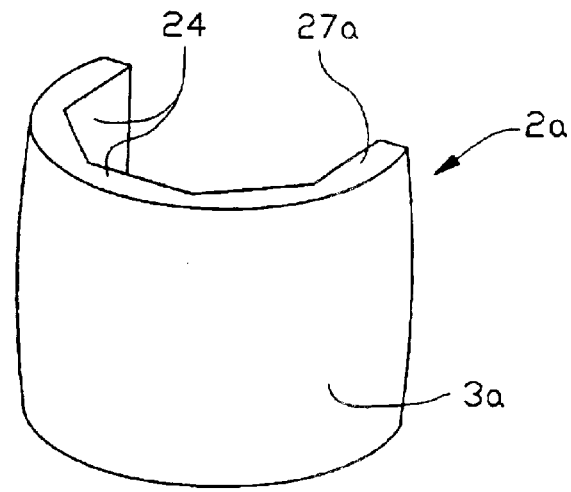
FIG. 8 is a perspective view of an alternative design of an ulnar component to that shown in FIGS. 1 and 2.
Figure 8A:
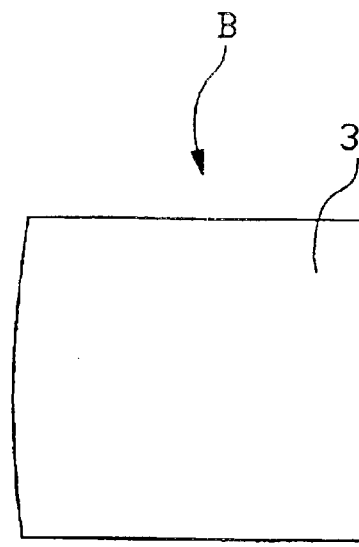
FIG. 8a is a front view of the surface of the ulnar component, of FIG. 8 that faces the radial component after implantation into the distal radioulnar joint.

As shown in FIGS. 1 and 8, the ulna component (2,2a) has a body (24) with a convex outer articulating surface (3). The outer surface (3) in FIG. 1, is in the form of a mainly semicylindrical envelope surface of circular cross section having a central axis (21). The orientation of the central axis is below described as being the same as the orientation of the axis of the natural ulna. In FIG. 8 is shown an alternative embodiment where the outer surface of the body (3a) is also convex in its longitudinal direction, i.e. having a generally barrel shape. The ulnar component (2,2a) has an inner surface (4), which is formed by a plurality, e.g. 5, of rectangular walls or panels (27) which are preferably aligned each at the same angle to the next adjacent wall, e.g. at about 135°.

A transection through the body (24) transverse to its longitudinal axis shows a horseshoe-shaped appearance. The design of the inner surface is that of a body formed of a number of juxtaposed and integrated to each other, mainly quadratic or rectangular panels or elements (27). The two extreme panels (27a) are normally parallel to each other and aligned to point away from the radius when the component is implanted on to the ulnar head.

The ulnar component (2) has a length L (FIG. 1) corresponding to the length of the natural ulnar head and to the size of the normal joint surfaces distally between the radius (6) and ulna (7). The ulnar component (2,2a) may be made of surgical stainless steel, but it can of course be made from other suitable materials as well known in the orthopedic art, such as pyrocarbon, ceramics, or composites. During the operation, the ulnar component is intended to be placed over the ulnar head (30), which has been appropriately resected.

The ulnar component (2) is manufactured in several different sizes and thicknesses, and this makes it possible to precisely adjust the size of the prosthesis relative to the size of the ulnar head which is to be resurfaced. It also makes it possible to adjust the tension across the joint by component size selection without changing the bony preparation.

As shown in FIGS. 3, 4, 7a and 7b, the radial component (1) has a concave (14) surface intended to face the ulnar component when inserted and articulate thereagainst. The concave surface may be a cylindrical surface, but in some embodiments, the surface may be concave also in the longitudinal direction of the radial component so as to interface with a barrel-shaped ulna component as seen in FIG. 8. On the side (28) opposing the concave side (14), the radial component (1) is usually supplied with at least one protruding part (5a, 5b, 13), which is intended to be received in a cut of the radius. The purpose of the protruding part is to secure the anchorage of the radial component to the radius. The protruding part could for example be formed as a pair of short posts or pegs, (5a, 5b) or a shelf or elongated tab (13). The radial component (1, 1a) is made in different thicknesses so that, by choosing the proper thickness, the joint and its ligaments can be adjusted to achieve optimal stability, desired tension and requisite range of motion.

Figure 7A:
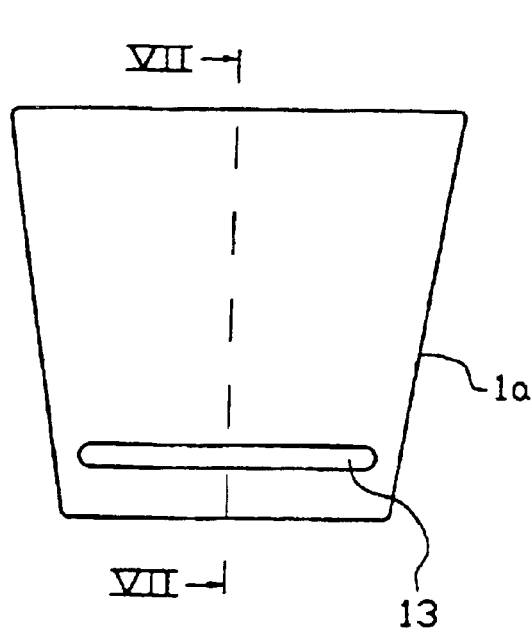
FIG. 7a is a front view of an alternative design of the radial component shown in FIGS. 3 and 4.
Figure 7B:
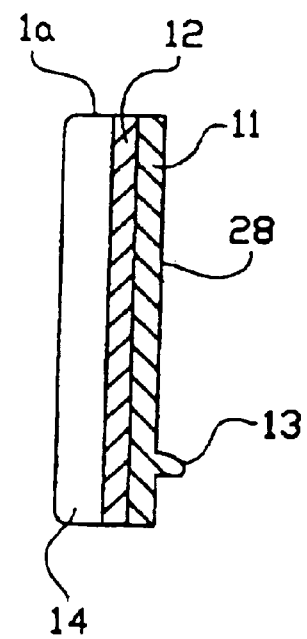

In the alternative embodiment shown in FIGS. 7a and 7b, the radial component 1a comprises a bearing plate portion (12) and a base plate portion (11). The latter is normally made from metal.

The radial component (1, 1a) is manufactured in various lengths and various thicknesses to make it possible, at each and every operation, to choose the right combination of length and thickness in relation to the size of the ulnar component (2) and the distance between the two cut surfaces of the radius and the ulnar head. The concave surface (14) of the radial component has a size and shape sufficient to allow the ulnar component to be able to continuously abut against the concave surface of the radial component during pronation or supination to and from the two extreme positions of rotation.

The radial and the ulnar component (1, 1a) and (2, 2a) are usually anchored with or without bone cement, e.g. polymethylmetacrylate (PMMA), to the radius (6) and ulna (7), respectively.

The radial and ulnar components are designed so that in the plane transverse to the longitudinal centreline (21), the radius of the convex external surface (3,3a) of the ulnar component is slightly less than that the corresponding radius of the concave surface of the radial component (14) (see FIG. 6b) in each part opposing each other during a full rotation of the arm. By this design of the convex (3,3a) and concave (14) surfaces, the ulnar head is assured to move relative to the concave radial surface (14) in both a rolling as well as a translatory movement.

In FIGS. 5a and 5b, it is shown schematically how the radius (6) and the ulna (7) are moved relative to each other when the forearm is turned 180 degrees, with the radius rolling around the ulna. According the invention, the radial component (1,1a) is designed to be placed in the distal part of the radius, and the ulnar component (2,2a) is designed to be placed on the facing part of the ulnar head.

Figure 6B:
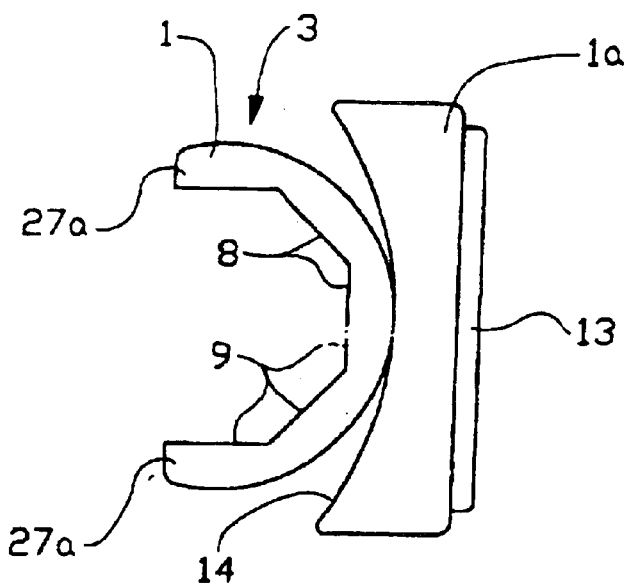

In FIGS. 6a and 6b, examples of the radial component (1) and the ulnar component (2) are shown in situ in position adjacent each other in the distal radioulnar joint. As best seen in FIG. 6b, the design of the radial component (1) and the ulnar component (2) effects the required rolling and translatory relative motion as the arm is rotated, during which rotation the ulna component, being radially attached to the ulna head, traces a relative path along the external concave surface (14) of the radial component.

To prepare the radius (6) and ulna (7) for the surface replacement, the radial and ulnar bones are cut by the operating surgeon. The radial cut leaves one flat surface, and the ulnar cut leaves a plurality, e.g. 5, flat surfaces in a prismatic array, which are fashioned to receive the radial (1,1a) and ulnar (2,2a) components. As previously noted, the radius (6) is prepared to receive the protruding part (13) or parts (5a, 5b) of the radial component which secure the anchoring of the radial component to the radial bone.

When the surface replacement is implanted according to the invention, the ulnocarpal ligaments and the triangular fibrocartilaginous complex (TFCC or the disc) are normally maintained; thereby, the passive compressive forces of the distal radioulnar joint are maintained. A radial cut thus cannot be made where these ligaments insert to the bone i.e. distal to the fovea on the radius or on the styloid of the ulna. The radial (6) and ulnar (7) cuts for the surface replacements (1, 1a; 2, 2a) thus are made immediately proximal to the insertion of the radioulnar ligaments. On the radial cut, a flat surface is formed with holes for the pegs (5a, 5b) or a slot to receive the protruding tab (13). On the ulna (7), rectangular angled cuts are prepared that will fit the contour (9) of the internal surface (2) of the ulnar component (2).

During the operation, the prepared ulnar end (7) can be pivoted to facilitate the cutting and then the mounting of the ulnar component (2,2a). For the radius, it is difficult to reach the whole cut bone surface, and the radial component may have to be slid down into place between the ulna and radius. The design with pegs (5) is pushed into prepared holes, or the tab (13) is pushed into a slot cut into the radius. As a result, the radial and the ulnar components are stabilized in their positions on the radius and ulna.

Although orientation of the distal joint surfaces of the radius and ulna may vary between individuals, a standard orientation of the joint surface or surfaces can be used for the radial and/or the ulnar components so long as they are properly positioned on radius and ulna respectively. The components are selected to fit by choosing from the varying lengths and thicknesses available. Adjustments are possible intraoperatively when the cuts are made and afterward by appropriate selection from components of varying thicknesses. In the embodiment where the outer surface of the ulnar component (3a) is convex also in the longitudinal direction, the standard orientation normally will be acceptable to the natural joint surface of the radial component. In a full replacement, both components are immediately mechanically stabile so postoperative motion can be started immediately by the patient.

Figure 2:
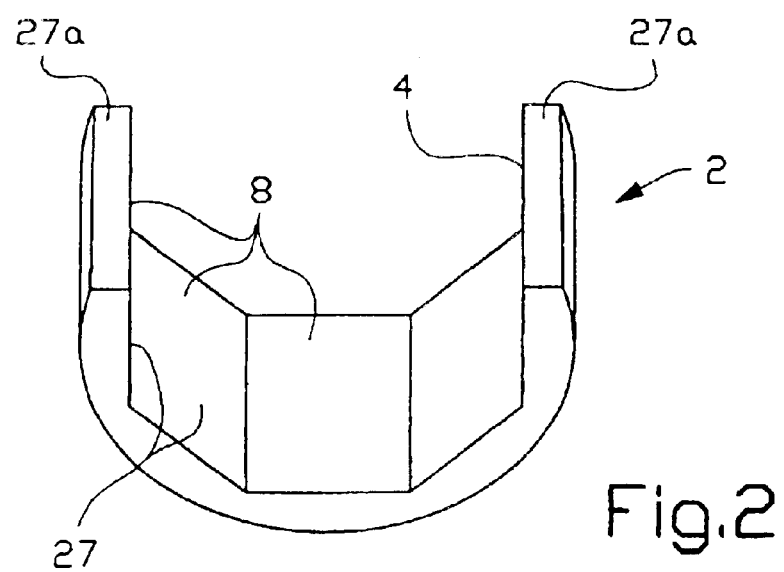
Figure 3:
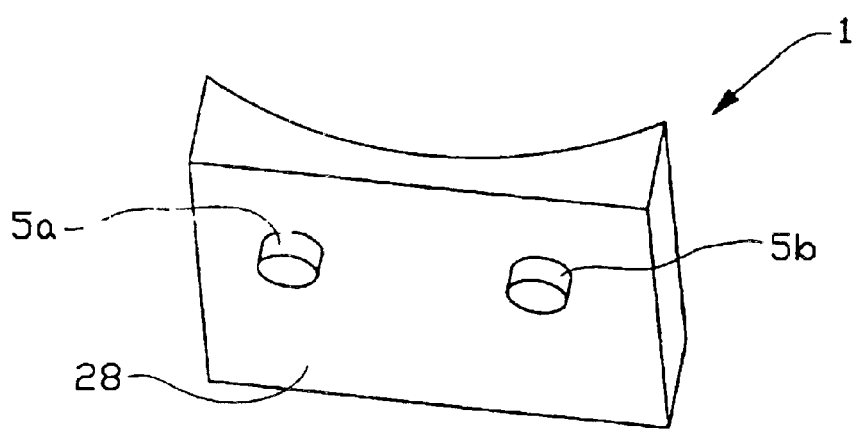
FIGS. 3 and 4 show a radial component embodying various features of the invention in two different perspectives, FIGS. 5a and b are schematic figures showing the ulna and radius with the hand in its extreme rotational positions i.e. supination 5a and pronation 5b.
Figure 4:
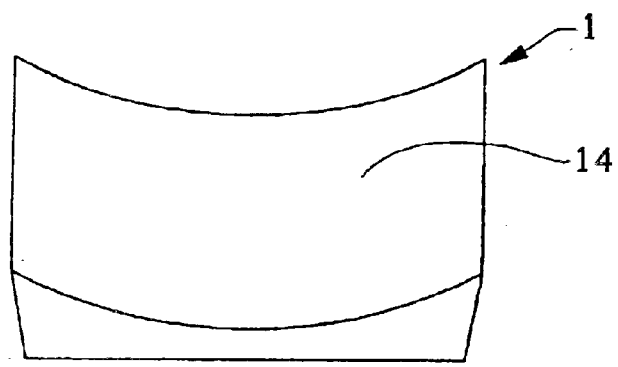
Figure 8B:
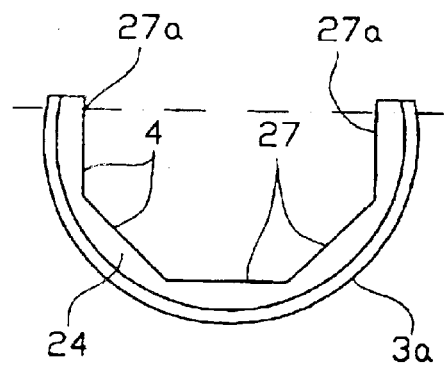
Figure 9:
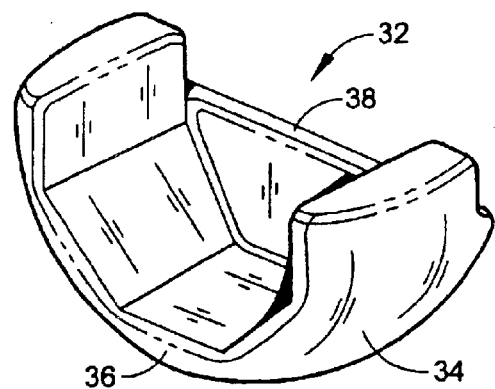
FIG. 9 is a perspective view of another alternative design of an ulna component embodying various features of the invention.
Figure 9A:
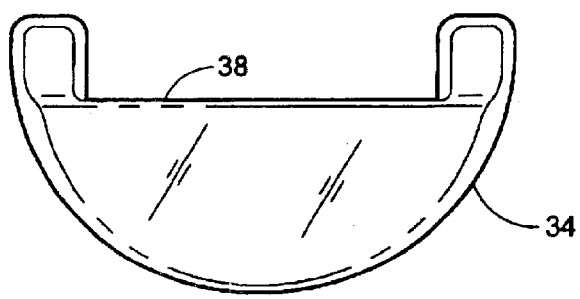
FIG. 9a is a top view of the ulna component of FIG. 9.
Figure 9B:
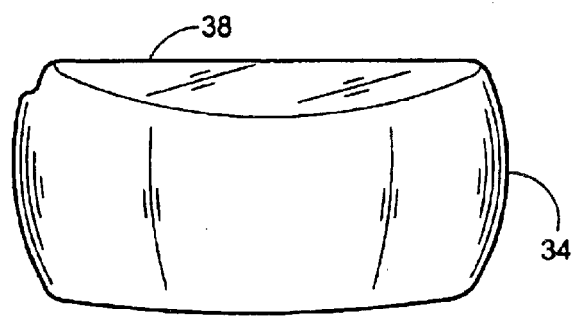
FIG. 9b is a front view of the ulna component of FIG. 9.
Figure 9C:
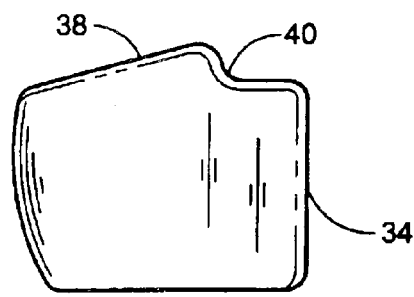
FIG. 9c is a right side view of the ulna component of FIG. 9.

Shown in FIGS. 9 through 9c is another alternative embodiment of an ulna component (32) which has an outer surface (34) and an interior surface (36). The outer surface (34) is preferably barrel-shaped, similar to the surface of the component (2a) illustrated in FIG. 8; however, it can be cylindrical if desired. The interior surface (34) is essentially the same as the interior surfaces of the components (2 and 2a) being formed from 5 flat wall sections of essentially rectangular shape which are arranged, as best seen in FIG. 8b, at obtuse angles to one another, which angles are preferably equal in size, e.g. about 135°. As a result the two outermost walls are parallel to each other, as are the panels 27a in FIG. 2. The interior shape may be referred to as that of a reverse prism.

The ulnar component (32) differs from the component (2a) in that it includes a cap section (38) in the form of a flange which extends obliquely up from the central portion of the upper end, spanning the two arms of the horseshoe arrangement as best seen in FIGS. 9 and 9a. At its terminus, the cap section is formed as a step or shoulder (40), dropping down to the upper edge of the component body at the location spaced slightly from the end edges. The presence of the cap more stably secures the ulnar component (32) on the resected end portion of the deteriorated ulna and can provide an improved prosthesis. One further advantage of the ulnar component (32) including the oblique cap section is the resurfacing of the articular portion of the distal ulnar head if required due to damaged articular cartilage.

Figure 10:
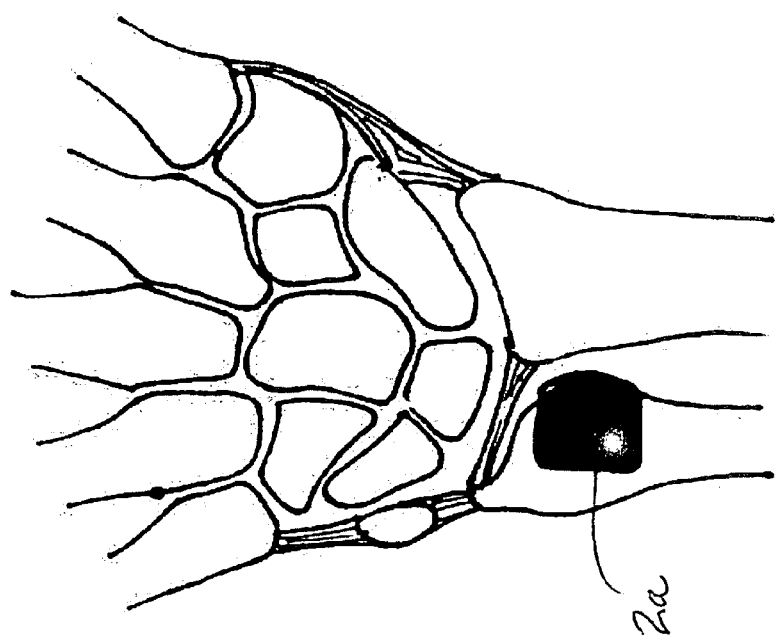
FIGS. 10 and 10a are schematic views of the distal radioulnar joint showing the implantation of the ulna component that was shown in FIG. 8 either as a part of a complete joint surface replacement or a singular replacement.
Figure 10A:
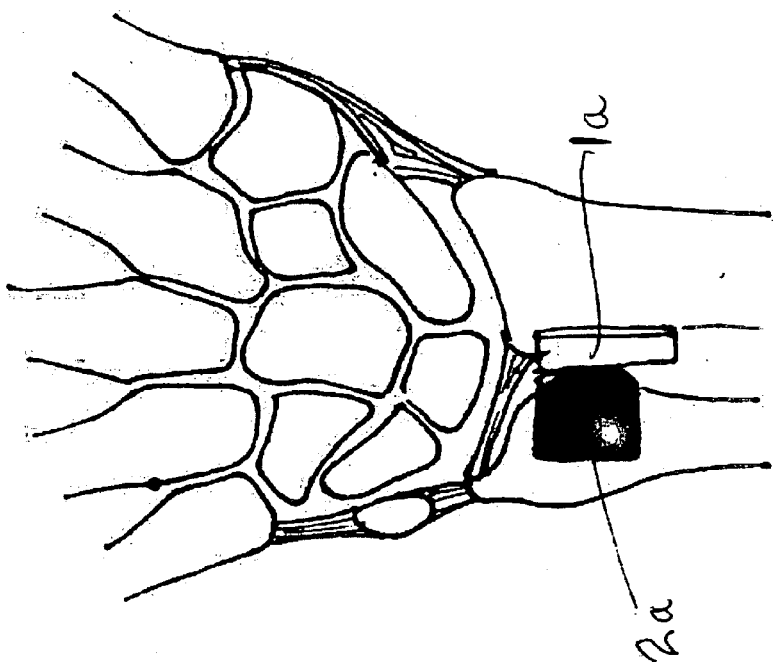

FIGS. 10 and 10a schematically show the installation in the wrist of an ulnar component such as that depicted in FIG. 8. In FIG. 10, the complete surface replacement is shown where the implanted ulnar component (2a) interfaces with an implanted radial component (1a). FIG. 10a illustrates a hemi replacement where there has been no deterioration of the radius and only an ulnar component (2a) is implanted. In such a situation, the ability of the surgeon to choose an ulnar component of appropriate size and thickness greatly facilitates the desired filling of the space adjacent the native radius and the achievement of stability in the resultant restructured joint without the need to repeat the surgical resection of the ulnar head.

Figure 11:
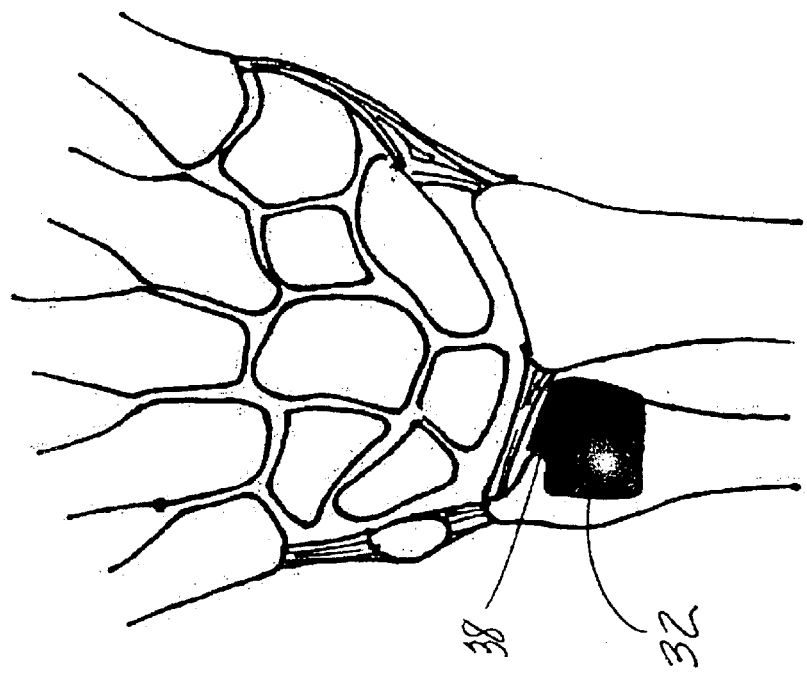
FIGS. 11 and 11a are schematic views similar to FIGS. 10 and 10a showing the ulna component of FIG. 9.
Figure 11A:
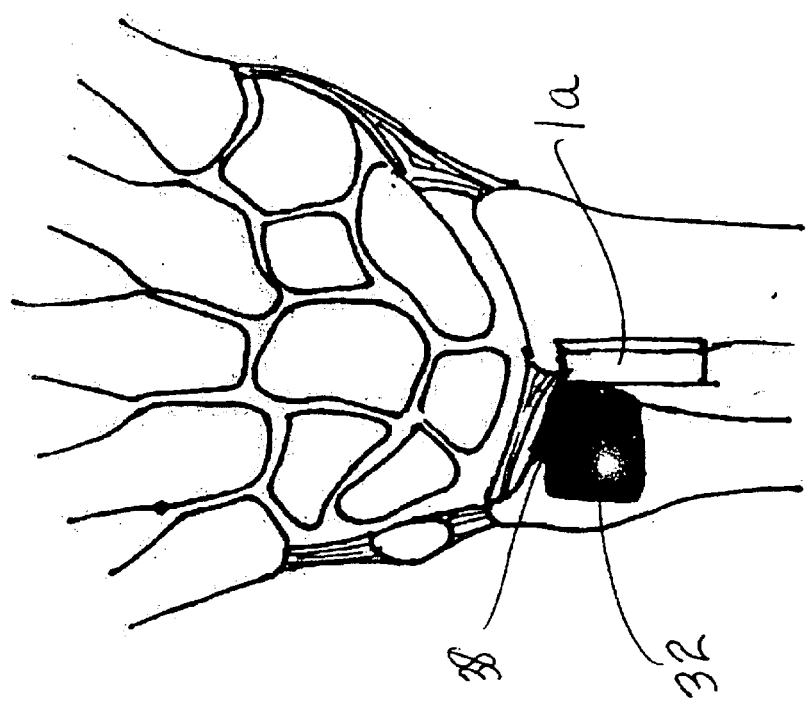

FIGS. 11 and 11a show similar illustrations of the implantation of an ulnar component (32) having the cap section (38) just described. In FIG. 11, it is shown as part of a complete surface replacement interfacing with an implanted radial component (1a), whereas in FIG. 11a, it is implanted singularly.

Figure 12:
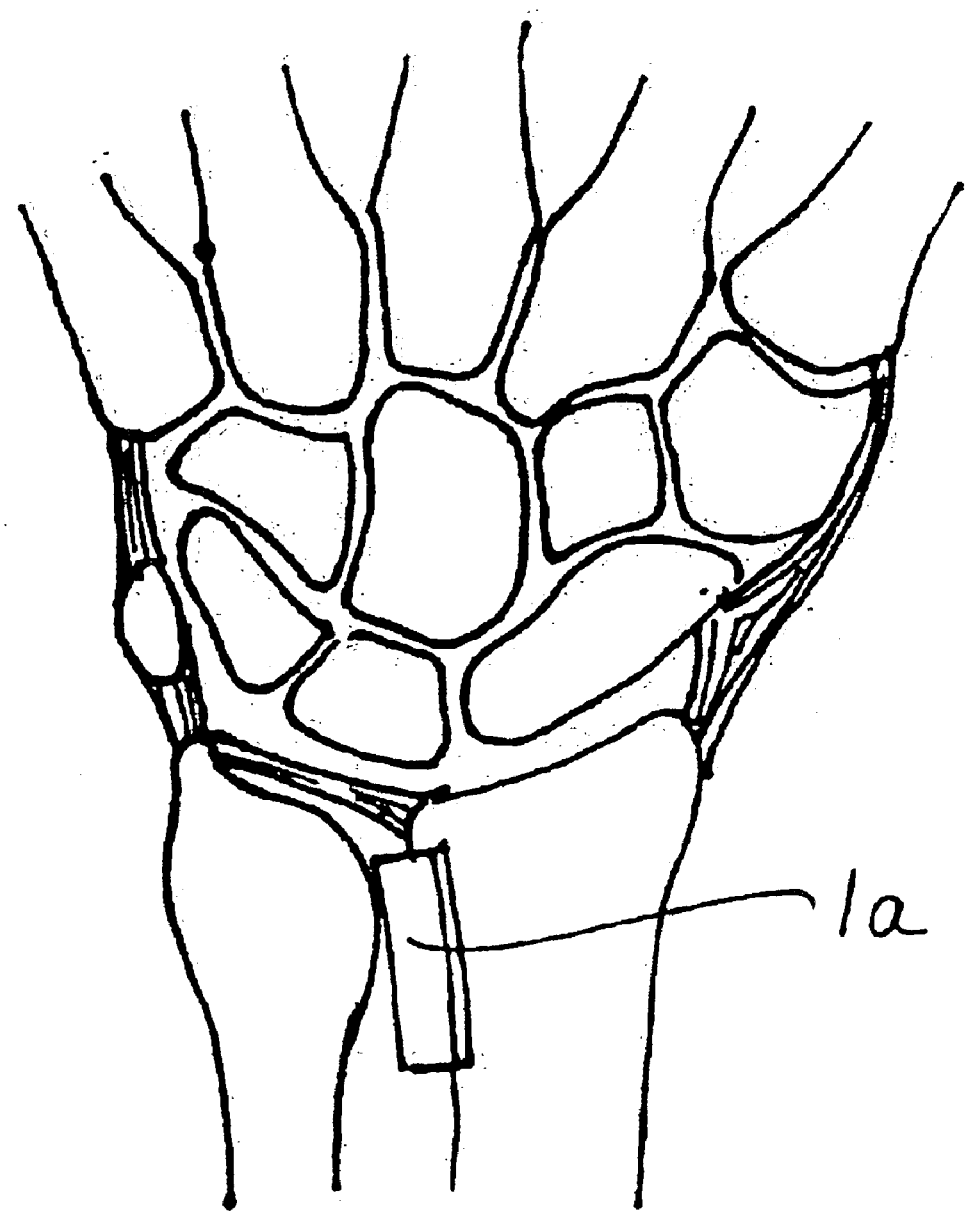
FIG. 12 is a schematic view similar to FIG. 10 showing the singular replacement of the radius surface.

FIG. 12 illustrates a hemi surface replacement where only the radial component (1a) is implanted to interface with the native ulna which has not suffered deterioration.

The description above demonstrates only a limited number of possible designs of the invention. The professional having ordinary skill in this art will realize that the invention hosts many modifications and embodiments that fall within the scope of the invention that is set forth in the following patent claims.

What is claimed is:

1. A surface replacement for the distal radioulnar joint of the wrist of a patient, characterized in that it comprises a radial component and an ulnar component, each of which is constructed to be placed radially on cut lateral regions near the distal ends of the radius and ulna, respectively, without disturbing the attachment of the radioulnar ligaments, so that they articulate against each other.

2. The surface replacement of claim 1, characterized in that the components are constructed to face each other, after implantation, throughout total rotational motion of the forearm and in that said cut lateral region of the radius is spaced from and does not alter the articular distal end of the radius.

3. A method of repairing the distal radioulnar joint by resecting the radius and the ulna of a patient and implanting the surface replacement according to claim 2, characterized in that the radial and ulnar components are anchored to the resected radius and ulna using bone cement.

4. The surface replacement of claim 1 characterized in that the ulnar component has a front convex outer surface and an inner surface of plurality of flat quadratic or rectangular walls angled at obtuse angles to one another.

5. The surface replacement according claim 1, characterized in that the ulnar component has a front convex outer surface and the radial component has a front concave surface intended to, after implantation, face toward the ulnar component and, during rotational movement of the distal radioulnar joint, bear against the outer convex surface of the ulnar component.

6. The surface replacement according to claim 5, characterized in that the radial component has an opposite rear surface having at least one protruding intended to be inserted into a receptacle cut in the radius.

7. The surface replacement of claim 6, characterized in that at least one protruding part comprises one or more pegs or an elongated tab.

8. The surface replacement of claim 5, characterized in that the radial component comprises a rear base anchoring plate and a front articulating plate which is affixed thereto.

9. A surface replacement for a member of the distal radioulnar joint at the wrist of a patient which comprises either a radial component or an ulnar component, each of which is constructed to be placed radially on a cut lateral surface near the distal end of the respective radius or ulna without removing the entire distal articular surface of thereof, wherein the ulnar component has a front convex outer surface and an inner surface of a plurality of flat quadratic or rectangular walls angled to each other and wherein the radial component has a front concave surface which is intended to, after implantation, face toward the ulna and against the outer convex surface of the ulna or the replacement ulnar component during rotational movement of the distal radioulnar joint.

10. The surface replacement of claim 9 wherein the ulnar component is constructed to resurface the radial portion of the distal ulna head without disturbing the styloid process of the ulna or the attachment of the radioulnar ligaments.

11. The surface replacement of claim 10 wherein a cap section is included which resurfaces a section of the articular surface of the distal ulna head, which section is opposite the styloid process.

12. A method of repairing the distal radioulnar (DRU) joint by resecting the lateral surface at a location near the distal end of the radius and/or the ulna at the wrist of a patient and implanting a surface replacement including at least one of a radial component and an ulnar component, wherein the ulnar component has a front convex outer surface and en inner surface of a plurality of flat quadratic or rectangular walls led to each other and wherein the radial component has a front concave surface so that, after implantation, in the repaired DRU joint the radial component faces toward and bears radially against the outer convex surface of the ulna or the replacement ulnar component during rotational movement of the distal radioulnar joint and/or the replacement ulnar component bears radially against either the radius or the replacement radial component.

13. A surface replacement for the distal radioulnar joint of the wrist of a patient, which replacement comprises a radial component and an ulnar component, each of which is constructed to be placed radially on cut lateral regions near the distal of the radius and ulna, respectively, so that they articulate against each other, said ulnar component having an inner surface that comprises a plurality of juxtapositioned walls that are integrated in a reverse prismatic array.

14. The surface replacement of claim 13, characterized in that the two outermost positioned walls are parallel to each other.

15. A surface replacement for the distal radioulnar joint of the wrist of a patient, which replacement comprises a radial component and an ulnar component, each of which is constructed to be placed radially on cut lateral regions near the distal ends of the radius and ulna, respectively, so that they articulate against each other, said ulnar component being constructed to resurface the radial portion of the distal ulnar bead without disturbing the styloid process of the ulna or the attachment of the radioulnar ligaments.

16. The surface replacement of claim 15 wherein said groups of different sized components have different thicknesses centrally and peripherally.

17. A surface replacement for a member of the distal radioulnar joint at the wrist of a patient, which replacement comprises either a radial component or an ulnar component, each of which is constructed to be placed radially on a cut lateral region near the distal end of the respective radius or ulna without removing the entire distal articular surface thereof, wherein the ulnar component has a front convex outer surface and an inner surface of a plurality of flat quadratic or rectangular walls angled to each other and wherein the radial component has a front concave surface which, after implantation, faces toward ulna and bears radially against the outer convex surface of the ulna or the replacement ulnar component during rotational movement of the distal radioulnar joint, and wherein either the radial component or ulnar component can be used singularly or together to the tension of the radioulnar ligaments to increase by increasing the distance between the distal heads of the radius ulna as a result of intraoperative selection of an appropriate radial or ulnar component from groups of such components which include a plurality of varying sizes.

18. The method of claim 17 where size of the convex curvature of the ulnar component, viewed normal to the long axis of the ulna is always smaller than the concave curvature of the radial component, viewed normal to the long axis of the radius, in all of the different size components.

19. A method of repairing the distal radioulnar (DRU) joint by resecting the lateral surface at a location near the distal end of the radius end/or the ulna at the wrist of a patient and implanting a surface replacement including at least one of a radial component and an ulnar component, wherein the ulnar component has a front convex outer surface and an inner surface of a plurality of flat quadratic or rectangular walls angled to each other and wherein the radial component has a front concave surface so that, after implantation, in the repaired DRU joint the radial component faces toward and bears radially the outer convex surface of the ulna or the replacement ulnar component during rotational movement of the distal radioulnar joint and/or the replacement ulnar component bears radially against either die radius or the replacement radial component and wherein either the radial or the ulnar component, in a case of distal radioulnar ligaments disruption, is used to allow intraoperative selection of an appropriate radial and/or ulnar component size from a plurality of different available sizes to cause the tension of the secondary stabilizers, such as the interosseus membrane, to increase by increasing the distance between the distal heads of the radius and the nine.

* * * * *

UNITED STATES PATENT AND TRADEMARK OFFICE
CERTIFICATE OF CORRECTION

PATENT NO. : 6,814,757 B2
DATED : November 9, 2005
INVENTOR(S) : Philippe Kopylov, Magnus Tagil and William F. Ogilvie It is certified that error appears in the above-identified patent and that said Letters Patent is hereby corrected as shown below:

Column 8,
Line 8, after "surface" insert -- region --;
Line 15, after "and" insert -- bear --;
Line 32, change "en" to -- an --;
Line 33, change "led" to -- angled --;
Line 60, change "bead" to -- head --;

Column 9,
Line 8, after "toward" insert -- the --;
Line 13, after "to" insert -- cause --;
Line 15, after "radius" insert -- and --;

Column 10,
Line 9, after "radially" insert -- against --;
Line 14, change "die" to -- the --;
Line 22, change "nine" to -- ulna --.

Signed and Sealed this

Third Day of January, 2006

JON W. DUDAS
*Director of the United States Patent and Trademark Office*

UNITED STATES PATENT AND TRADEMARK OFFICE
CERTIFICATE OF CORRECTION

PATENT NO.     : 6,814,757 B2
DATED          : November 9, 2004
INVENTOR(S)    : Philippe Kopylov, Magnus Tagil and William F. Ogilvie It is certified that error appears in the above-identified patent and that said Letters Patent is hereby corrected as shown below:

Column 8,
Line 8, after "surface" insert -- region --;
Line 15, after "and" insert -- bear --;
Line 32, change "en" to -- an --;
Line 33, change "led" to -- angled --;
Line 60, change "bead" to -- head --;

Column 9,
Line 8, after "toward" insert -- the --;
Line 13, after "to" insert -- cause --;
Line 15, after "radius" insert -- and --;

Column 10,
Line 9, after "radially" insert -- against --;
Line 14, change "die" to -- the --;
Line 22, change "nine" to -- ulna --.

This certificate supersedes Certificate of Corrections issued January 3, 2006.

Signed and Sealed this

Twenty-first Day of February, 2006

JON W. DUDAS
*Director of the United States Patent and Trademark Office*